United States Patent [19]

Kleiner et al.

[11] Patent Number: 5,407,969
[45] Date of Patent: Apr. 18, 1995

[54] ACYL-(2'-HYDROXYBIPHENYL-2-YL)-PHOSPHINIC ACID SALTS, THEIR PREPARATION AND USE

[76] Inventors: Hans-Jerg Kleiner, Altkönigstrasse 11a, D-6242 Kronberg 2; Joachim Gersdorf, Philipp-Holl-Strasse 26, D-6200 Wiesbaden; Udo Bastian, Backhausfeld 25, D-4030 Ratingen, all of Germany

[21] Appl. No.: 50,347
[22] PCT Filed: Oct. 9, 1991
[86] PCT No.: PCT/EP91/01919
 § 371 Date: Apr. 16, 1993
 § 102(e) Date: Apr. 16, 1993
[87] PCT Pub. No.: WO92/06983
 PCT Pub. Date: Apr. 30, 1992

[30] Foreign Application Priority Data

Oct. 19, 1990 [DE] Germany .................. 40 33 215.2

[51] Int. Cl.$^6$ .............................................. C08F 2/46
[52] U.S. Cl. .................................. 522/14; 522/64; 562/24
[58] Field of Search ................ 562/24; 522/64, 14

[56] References Cited

U.S. PATENT DOCUMENTS

| | | | |
|---|---|---|---|
| 3,702,878 | 11/1972 | Saito | 562/24 |
| 4,719,297 | 1/1988 | Henne et al. | 522/64 |
| 5,008,426 | 4/1991 | Kleiner et al. | 558/82 |
| 5,096,935 | 3/1992 | Kleiner et al. | 522/64 |

FOREIGN PATENT DOCUMENTS 810642  3/1959  United Kingdom .................. 562/24

*Primary Examiner*—Mark A. Chapman

[57] ABSTRACT

The invention relates to acyl-(2'-hydroxydiphenyl-2-yl)-phosphinic acid salts of formula (I)

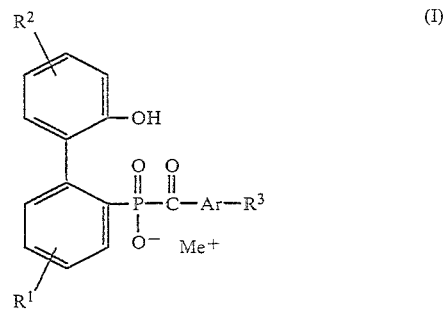

in which each of the radicals $R^1$, $R^2$ and $R^3$ may be included singly or multiply and in which $R^1$ and $R^2$ are mutually independently hydrogen, an alkyl or alkoxy radical with 1 to 6 carbon atoms or halogen with an atomic number of 9 to 35; $R^3$ means the same as $R^1$ or $R^2$; Ar is an aromatic hydrocarbon radical with 6 to 10 carbon atoms; and Me is a cation of at least one alkaline metal or $N(R^4)_4+$ in which the radicals $R^4$ are the same or different and stand for an alkyl radical with 1 to 6 carbon atoms. The invention also relates to a process for producing these compounds (I) and their use as photoinitiators in photopolymerisable materials, preferably on an aqueous basis.

15 Claims, No Drawings

ACYL-(2'-HYDROXYBIPHENYL-2-YL)-PHOSPHINIC ACID SALTS, THEIR PREPARATION AND USE

A number of photoinitiators based on acylphosphinic acid esters and acylphosphane oxides are already known (cf. EP Published Specification 7508). EP Published Specification 304 782 furthermore describes acyl-(6H)-dibenz[c,e][1,2]-oxaphosphorine 6-oxides for this purpose. However, these compounds are not suitable as photoinitiators in aqueous, photopolymerized compositions. Acylphosphonic acid salts are indeed already described in EP Published Specification 62 839 for use as photoinitiators in aqueous systems; a disadvantage here, however, is the expensive preparation of these salts, during which, for example, alkyl oxides occur as by-products.

The object of the invention was now to provide novel acyl-phosphorus compounds which do not have the disadvantages of the prior art and which be prepared, in particular, in a manner which is particularly simple industrially, but nevertheless meet the high requirements demanded in practice and also are particularly suitable for use in aqueous photopolymerizable compositions. The invention relates to a process for the preparation of acyl-(2'-hydroxybiphenyl-2-yl)-phosphinic acid salts of the formula (I)

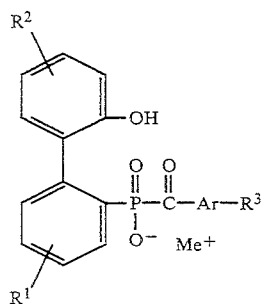

in which each of the radicals $R^1$, $R^2$ and $R^3$ can be present once or several times, preferably not more than three times, and in which $R^1$ to $R^3$ independently of one another are hydrogen, an alkyl or alkoxy radical having in each case 1 to 6, preferably 1 to 4, carbon atoms or halogen having an atomic number of 9 to 35, preferably chlorine, Ar is an aromatic hydrocarbon radical having 6 to 10 carbon atoms and Me is a cation of at least one alkali metal, preferably having an atomic number of 3 to 19, or $N(R^4)_4^+$, in which the radicals $R^4$ are identical or different and are an alkyl radical having in each case 1 to 6, preferably 1 to 4, carbon atoms.

These compounds (I), which have a very good reactivity as photoinitiators, are surprisingly readily water-soluble, although their molecule mainly comprises hydrophobic regions (hydrocarbon radicals). Furthermore, the very reactive

grouping in them is surprisingly stable to hydrolysis.

Compounds (I) which are preferably prepared according to the invention are those which have at least one of the following features:

a) at least one of the two radicals $R^1$ and $R^2$, and preferably both these radicals, is/are hydrogen, b) the radical $R^3$ is hydrogen or at least one alkyl radical, preferably one to three alkyl radicals, in particular methyl radicals, and c) the radical Ar is a benzene ring.

Alkyl or alkoxy in the radicals $R^1$ to $R^3$ is, in particular, methyl or ethyl.

Examples of alkyl groups are methyl, ethyl, propyl, isopropyl and the various butyl radicals, the two former, and especially methyl, being preferred. Preferred examples of alkoxy radicals are methoxy and ethoxy, in particular methoxy.

In addition to the compounds (I) described in the examples, the following may also be mentioned here as examples: the sodium salt of (4-methyl-benzoyl)(2'-hydroxybiphenyl-2-yl)-phosphinic acid, the sodium salt of (2,6-dimethyl-benzoyl)(2'-hydroxybiphenyl-2-yl)-phosphinic acid, the lithium salt of (4-ethyl-benzoyl)(2-'hydroxybiphenyl-2-yl)-phosphinic acid, the lithium salt of (2,6-dichlorobenzoyl)(2'-hydroxybiphenyl-2-yl)-phosphinic acid and the potassium salt of (2,6-dichlorobenzoyl)(2'-hydroxybiphenyl-2-yl)-phosphinic acid.

The invention also relates to a process for the preparation of the compounds (I), which comprises reacting 6-acyl-(6H)-dibenz[c,e][1,2]oxaphosphorine 6-oxides of the formula (II)

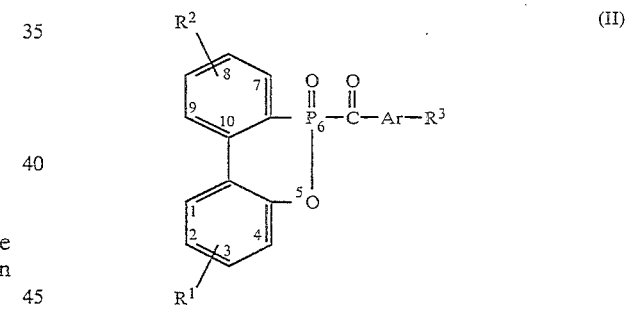

in which $R^1$ to $R^3$ and Ar have the meaning given in the above formula (I), with salts of carbonic acid of the formulae $MeHCO_3$ (III) or $Me_2CO_3$ (IV), in which Me in each case has the meaning according to formula (I), the reaction being carried out in the presence of water in the case of the carbonates (IV) (in this context, see also the attached sheet of formulae).

Surprisingly, the compounds (I) are obtained in good yields by this process.

The reaction is expediently carried out in the presence of a diluent, such as, for example, water, which must in any case be present in the case of the carbonates (IV). Other possible diluents are the usual, preferably water-miscible, polar organic solvents, such as ethers and glycol ethers, for example diethyl ether, 1,2-dimethoxyethane, ethylene glycol dibutyl ether, tetrahydrofuran or dioxane; ketones, for example acetone, methyl ethyl ketone, methyl isobutyl ketone, cyclohexanone and the like; esters, for example ethyl acetate, butyl acetate, ethylene glycol monoethyl acetate and methoxypropyl acetate; N-methyl-pyrrolidone; mono- or polyhydric alcohols, such as methanol, ethanol, isopropanol, butanol, ethylene glycol monoethyl(butyl) ether and the like; and furthermore acetonitrile, formamide and dimethylformamide. These solvents can also be employed as a mixture with one another.

Preferred solvents here are the lower alcohols, in particular isopropanol.

Other preferred diluents are mixtures of organic solvents, in particular lower alcohols, and water, the water content in general being 5 to 60% by weight, preferably 15 to 40% by weight, based on the mixture.

The process according to the invention is expediently carried out by gradually metering the second component into one component, carbon dioxide being split off. Compound (II) is preferably initially introduced into the reaction vessel here. The reaction is in general carried out at temperatures from 20° to 80° C. preferably 40° to 70° C., and under normal pressure. However, in special cases, even higher temperatures and reduced or increased pressure can also be used.

Preferred possible bicarbonates (III) and carbonates (IV) are those of lithium, sodium or potassium or corresponding mixtures.

The compounds (II) employed as starting substances for the process according to the invention are known from EP Published Specification 304 782 and can be prepared in a simple manner. Reference is made here to this literature source.

The compounds (I) obtained are worked up in the customary manner, for example by crystallization.

The compounds (I) according to the invention exhibit a very good reactivity as photoinitiators for photopolymerization of unsaturated compounds having at least one C—C multiple bond and mixtures thereof with one another and with additives. A considerable advantage of these compounds (I) according to the invention here is also their good solubility, dispersibility and/or compatibility in or with both polar and non-polar media. As a result, for example in the case of their use in recording compositions or printing inks, the non-exposed and non-crosslinked portions of a layer of the photopolymerizable recording compositions can be washed out after their imagewise exposure, or good mixing of the salts in aqueous UV paint or printing ink systems is achieved.

The present invention therefore also relates to photopolymerizable compositions which comprise the compounds (I) according to the invention.

The photopolymerizable compositions according to the invention, for example for the production of printing plates and relief forms and for the production of coating systems and printing inks which can be cured by irradiation, comprise as essential constituents at least one binder, at least one low molecular weight polymerizable monomer, at least one photoinitiator, and if appropriate a diluent and customary additives. The term "photopolymerizable compositions" here is intended to include corresponding coating agents, paints, printing inks and recording materials, and furthermore photopolymerizable, aqueous solutions, dispersions and emulsions as well as grouting, filler or sealing compositions.

At least one compound (I) is employed as a photoinitiator in the photopolymerizable compositions according to the invention, the amount thereof in general being 0.01 to 20% by weight, preferably 0.1 to 5% by weight, based on the photopolymerizable composition. Mixtures of compounds (I) can also be used.

If appropriate, these photoinitiators (I) can also be combined with known accelerators which eliminate the inhibiting influence of atmospheric oxygen on the photopolymerization and are usually employed in amounts of 0.1 to 15% by weight, preferably 1 to 5% by weight, based on (I). Such accelerators or synergists are, above all, amines, preferably tertiary amines. Examples which may be mentioned here are: diethanolamine, N-methyldiethanolamine, N-phenyldiethanolamine, N,N-dimethyl-ethanolamine, triethylamine, triethanolamine, ethyl p-dimethylaminobenzoate, benzylmethylamine, benzyldimethylamine, dimethylaminoethyl acrylate, N-methyl-N-phenylglycine and analogous compounds known to the expert. Aliphatic and/or aromatic halides furthermore can be used to accelerate the curing, such as 2-chloromethylnaphthalene and 1-chloro-2-chloromethylnaphthalene, as well as agents which form free radicals, such as peroxides and azo compounds.

According to another advantageous embodiment, the compounds (I) according to the invention can also be employed in combination with known photoinitiators, such as are described, for example, in EP Published Specification 304 782, in all proportions, for example 0.5:1 to 30:1, preferably 0.8:1 to 10:1, and in particular 1:1 to 3:1. Such suitable initiators are, for example, aromatic ketones and functional derivatives thereof, such as ketals, for example benzyl dimethyl ketal, 2-hydroxy-2-methyl-1-phenylpropan-1-one, diethoxyacetophenone, benzophenone and derivatives of thioxanthone, or mixtures of these.

A procedure is expediently followed here in which the commercially available initiators, the thioxanthones, benzophenones, hydroxyalkylphenones or also acylphosphane oxides, are dissolved in the binder/monomer mixture, this mixture is emulsified or dispersed in water, and the aqueous solution of the salt according to the invention is then added, while stirring. If the solubility of this salt allows, this can also be dissolved in 100% systems, i.e. solvent-free systems.

The total content of these combinations is in general between 0.01 and 20% by weight, preferably 0.1 to 5% by weight, based on the weight of the total polymerizable composition.

The salts (I) according to the invention can also be combined with the known photoinitiators such that the corresponding emission range of the UV lamp corresponds completely to the absorption range of the initiator combination (for example 300–420 nm or 200–420 nm).

A particular advantage of these photoinitiator combinations is that a significant increase in the curing rate and a better hardness of the cured films are achieved. Another advantage of these photoinitiator combinations is that they are inexpensive. Furthermore, pigmented aqueous or 100% systems can also be cured with the aid of these combinations.

Suitable photopolymerizable monomers are the usual compounds and substances having polymerizable C—C double bonds which are activated by, for example, aryl, carbonyl, amino, amide, amido, ester, carboxyl or cyanide groups, halogen atoms or C—C double or C—C triple bonds. Examples which may be mentioned are vinyl ethers and vinyl esters, styrene, the various vinyltoluenes, allyl ether, acrylic and methacrylic acid and esters thereof with mono- and/or polyhydric alcohols, and nitriles or amides thereof, and furthermore mono- or diacrylates or -methacrylates of oligomeric glycols, as well as acrylic and methacrylic acid esters of the reaction products of polyhydric alcohols with glycols, such as trimethylolpropane triethoxytriacrylate, maleic and fumaric esters and N-vinylpyrrolidone, N-vinylcaprolactam, N-vinylcarbazole and allyl esters, such as diallyl phthalate.

A large number of soluble organic polymers can be employed as binders in the photopolymerizable compositions according to the invention. Examples of these which may be mentioned are: polyamides, in particular alcohol-soluble copolyamides, such as are described in FR Patent 1 520 856, cellulose derivatives, in particular aqueous-alkaline cellulose derivatives which can be washed off, vinyl alcohol polymers, as well as polymers and copolymers of vinyl esters of saturated aliphatic monocarboxylic acids having 2 to 4 carbon atoms, such as vinyl acetate or vinyl propionate, with a varying degree of hydrolysis, polyurethanes, polyether-urethanes and polyester-urethanes, polyvinylacetals, epoxy resins, polyacrylic acid esters, polymethacrylic acid esters, polyesters, in particular unsaturated polyester resins, such as are described below, alkyd resins, polybutadiene, polyisoprene, isoprene/styrene block copolymers and other elastomers, and copolymers of the monomers which form the homopolymers listed.

Of the polyesters of a linear or branched nature prepared by reaction of unsaturated and, if appropriate, saturated polybasic carboxylic acids with polyhydric alcohols, those having a relatively high acid number, and in particular an acid number of between 75 and 160, are preferred, since, in the compositions, they lead to a good dispersibility or solubility in alkaline-aqueous developer solvents.

Suitable unsaturated polyester resins are, for example, those which are prepared by reaction of $\alpha,\beta$-olefinically unsaturated dicarboxylic acids, such as maleic acid, fumaric acid or itaconic acid, if appropriate mixed with saturated or aromatic dicarboxylic acids, such as adipic acid, ortho-, iso- or terephthalic acid or tetrahydrophthalic acid, or with alkanediols, such as ethylene glycol, propylene glycol, butanediol, neopentyl glycol or oxyalkylated bisphenol A; and furthermore epoxide-acrylates, prepared from acrylic or methacrylic acid and aromatic or aliphatic diglycidyl ethers, and urethaneacrylates, for example prepared from hydroxyalkyl acrylates and polyisocyanates, as well as polyesteracrylates, for example prepared from saturated polyesters containing hydroxyl groups and acrylic or methacrylic acid.

Binders which are water-insoluble but soluble or at least swellable in aqueous-alkaline solutions can likewise be used, since layers comprising such binders can be developed with aqueous-alkaline developers. Such binders can contain, for example, the following groups: —COOH, $PO_3H_2$, —$SO_2NH$—, —$SO_2$—NH—$SO_2$— and —$SO_2$—NH—CO—. Examples of these which may be mentioned are: maleate resins, polymers of $\beta$-(methacryloyloxy)-ethyl N-(p-tolyl-sulfonyl)carbamate and copolymers of this and similar monomers with other monomers, vinyl acetate/crotonic acid, styrene/maleic anhydride, alkyl methacrylate/methacrylic acid, higher alkyl methacrylates and methyl methacrylate and/or styrene or acrylonitrile.

Mixtures based on water-soluble binders are particularly advantageously employed, since the compounds according to the invention can be combined particularly readily with these and allow convenient and environment-friendly coating from an aqueous solution. Examples of such binders are polyvinyl alcohol, partly hydrolyzed polyvinyl acetals and vinyl acetate copolymers, partly hydrolyzed vinyl acetate graft polymers, such as are described in DE-A 37 32 089, polyvinyl ethers, polyvinylpyrrolidone, polyacrylamide, polydimethylacrylamide, polyethylene oxide, polyvinylmethylformamide, polyvinylmethylacetamide and water-soluble naturally occurring polymers.

The compositions according to the invention comprise mainly, i.e. to the extent of more than 50, and preferably to the extent of 70 to 100% by weight, the photo-initiator-comprising mixture of monomers and binders. The content of polymeric binders in this mixture is in general about 45 to 95, and in particular 45 to 65% by weight, based on the sum of the amounts of monomers and binders.

Saturated and/or unsaturated polymers and other additives, such as inhibitors of thermal polymerization, paraffin, pigments, dyestuffs, peroxides, flow auxiliaries, fillers, dulling agents and glass fibers, as well as stabilizers against thermal or photochemical degradation, can additionally be added in a manner which is known per se to the photopolymerizable compositions, the composition of which for the particular intended use is familiar to the expert. The nature and amount of the additions depend on the particular intended use. The same also applies to the nature and amount of any diluent present.

Processing of the photopolymerizable compositions can be carried out in the customary manner, and depends on whether the composition is liquid or solid. It is carried out by exposure to light, for example actinic light. Thereafter, for example for production of relief printing forms or photoresists, the non-exposed portions of the layer of the recording compositions are removed mechanically in the customary manner or washed out with a suitable developer solvent, and the resulting forms are dried, and in some cases also finally exposed in full.

For processing aqueous systems which can be cured by high-energy radiation, before the irradiation with, for example, actinic radiation, the water must be removed from the film to be cured, since otherwise only incomplete curing of the material takes place. This is as a rule effected by using IR dryers or drying ovens, for example circulating air dryers.

Aqueous solutions or emulsions of suitable monomers can likewise be photopolymerized using the compounds (I) according to the invention in a known manner, for example as described in EP Published Specification 62 839.

The radiation sources used for the light which triggers the polymerization of such systems are in general those which preferably emit light in the absorption range of the compounds (I) according to the invention, i.e. between 300 and 450 nm. Mercury low pressure lamps and medium pressure and high pressure lamps, and (super-actinic) tubular lamps or pulse lamps are particularly suitable. If appropriate, the lamps mentioned can be doped. Radiation sources which emit approximately monochromatic light furthermore can also be employed.

The following examples illustrate the invention in more detail.

EXAMPLES

I. Preparation Examples

1. The potassium salt of (2-methyl-benzoyl)-(2'-hydroxybiphenyl-2-yl)-phosphinic acid 50.1 g (0.15 mol) of 6-(2-methyl-benzoyl)-(6H)-dibenz[c,e][1,2]-oxaphosphorine 6-oxide were dissolved in 218 g of isopropanol and 45 ml of water at 60° C. 15 g (0.15 mol) of potassium bicarbonate were then added in portions in the course of 30 minutes, carbon dioxide being evolved. The mixture was subsequently stirred at 60° C. for 2 hours and then filtered with suction. 39 g (67% of theory) of the abovementioned compound with a decomposition point about 280° C. were obtained.

$C_2H_{10}KO_4P$ (390) calculated: 61.54% C 4.10% H 10.00% K 7.95% P found: 61.5% C 4.0% H 9.5% K 7.8% P 2. The lithium salt of (2-methyl-benzoyl) (2'-hydroxybiphenyl-2-yl)-phosphinic acid 39 g (0.117 mol) of 6-(2-methyl-benzoyl)-(6H)dibenz[c,e][1,2]-oxaphosphorine 6-oxide were dissolved in 170 g of isopropanol and 35 ml of water at 60° C. 4.3 g (0.0584 mol) of lithium carbonate were now added in the course of 15 minutes, carbon dioxide being evolved. The mixture was stirred at 60° C. for 2 hours and then filtered with suction. 23.7 g were obtained. After concentration, a further 13.3 g were obtained from the mother liquor. A total of 37 g (89% of theory) of the abovementioned compound of decomposition point about 250° C. were obtained.

$C_{20}H_{16}LiO_4P$ (358) calculated: 67.04% C 5.59% H 1.96% Li 8.66% P found: 67.1% C 5.6 % H 1.7 % Li 8.3 % P 3. The sodium salt of (2,4,6-trimethyl-benzoyl)-(2'-hydroxybiphenyl-2-yl)-phosphinic acid 108.6 g (0.3 mol) of 6-(2,4,6-trimethyl-benzoyl)-(6H)-dibenz[c,e][1,2]-oxaphosphorine 6-oxide were dissolved in 435 g of isopropanol and 90 g of water at 60° C. 25.2 g (0.3 mol) of sodium bicarbonate were now added in portions at this temperature in the course of 30 minutes, carbon dioxide being evolved.

The mixture was then subsequently stirred at 40°-60° C. for 8 hours. After filtration with suction, 63.5 g were obtained; a further 50 g were to be obtained from the filtrate after concentration. A total of 113.5 g (94% of theory) of the abovementioned compound of decomposition point 230°-237° C. were obtained.

$C_{22}H_{20}NaO_4P$ (402) calculated: 65.67% C 4.97% H 5.72 % Na 7.71% P found: 65.5% C 4.8% H 5.2% Na 6.8% P 4. The potassium salt of (2,4,6-trimethyl-benzoyl)-(2'-hydroxybiphenyl-2-yl)-phosphinic acid 36.2 g (0.1 mol) of 6-(2,4,6-trimethyl-benzoyl)-(6H)-dibenz[c,e][1,2]-oxaphosphorine 6-oxide were dissolved in 145 g of isopropanol and 30 ml of water at 60° C. 10 g (0.1 mol) of potassium bicarbonate were now added in the course of 10 minutes, during which carbon dioxide was evolved. On subsequent stirring, the abovementioned compound crystallized out. 39.5 g (95% of theory) of decomposition point about 300° C. were obtained.

$C_{22}H°KO_4P$ (418) calculated: 63.16% C 4.79% H 9.33% K 7.42% P found: 63.1% C 4.8% H 9.1% K 7.3% P 5. The lithium salt of (2,4,6-trimethyl-benzoyl)-(2'-hydroxybiphenyl-2-yl)-phosphinic acid 36.2 g (0.1 mol) of 6-(2,4,6-trimethyl-benzoyl) (6H)-dibenz[c,e][1,2]-oxaphosphorine 6-oxide were dissolved in 145 g of isopropanol and 30 ml of water at 60° C. 3.7 g (0.05 mol) of lithium carbonate were now added in portions, carbon dioxide being evolved. The temperature was then increased to 75° C. and the mixture was subsequently stirred for 5 hours. It was then filtered and the filtrate was largely freed from solvent. 37 g (96% of theory) of the above mentioned compound of decomposition point about 135° C. were obtained.

$C_{22}H_{20}LiO_4P$ (386) calculated: 68.39% C 5.18% H 1.81% Li 8.03% P found: 68.4% C 5.2% H 1.7% Li 7.9% P 6. The lithium salt of (1-(2-methyl-naphthoyl))-(2'hydroxybiphenyl-2-yl)-phosphinic acid 32.6 g (0.085 mol) of 6-(1-(2-methyl-naphthoyl))(6H)-dibenz[c,e][1,2]-oxaphosphorine 6-oxide were dispersed in a mixture of 123 g of isopropanol and 25 g of water. The reaction mixture was then heated to the reflux temperature, while stirring. 3.15 g (0.0425 mol) of lithium carbonate were now added in portions in the course of one hour, carbon dioxide being evolved. Thereafter, the mixture was subsequently stirred for two hours and then largely freed from the solvent in vacuo. 31 g (89% of theory) of the abovementioned compound of melting point 120°–130° C. and decomposition point 160° C. remained.

$C_2H_{Li}O_4P$ (408) calculated: 70.59% C 4.41% H 1.72% Li 7.60% P found: 70.5% C 4.4% H 1.6% Li 7.3% P 7. The potassium salt of (1-(2-methyl-naphthoyl))-(2'-hydroxybiphenyl-2-yl)-phosphinic acid 32.6 g (0,085 mol) of 6-(1-(2-methyl-naphthoyl))-6H)-dibenz[c,e][1,2]-oxaphosphorine 6-oxide were added to a mixture of 150 ml of tetrahydrofuran and 25 ml of water and the mixture was heated to 60° C., while stirring. 8.5 g (0.085 mol) of potassium bicarbonate were now added in portions in the course of one hour. The mixture was subsequently stirred for 1.5 hours, and then cooled and filtered with suction. 32.2 g (86% of theory) of the above-mentioned compound of decomposition point 280° C. were obtained.

$C_{24\ 2}H_{18}KO_4P$ (440) calculated: 65.46% C 4.09% H 8.86% K 7.05% P found: 65.1% C 4.1% H 8.7% K 6.9% P II. Use Examples 1. 145.5 parts by weight of an internally plasticized vinyl alcohol copolymer having a viscosity of 4 mPas in 4% strength aqueous solution at 20° C. and an ester number of 150 were dissolved by stirring in 147 parts by weight of water at 90° C. After cooling to 60° C., 95.8 parts by weight of diethylene glycol monoacrylate, 5.3 parts by weight of trimethylolpropane triacrylate, 2.1 parts by weight of 2,6-di-tert.-butyl-4-methylphenol and 5.3 parts by weight of the potassium salt of (2-methyl-benzoyl)-(2'-hydroxybiphenyl-2-yl)-phosphinic acid according to Preparation Example 1 were added, while stirring. The homogeneous solution was applied to a 0.125 mm thick polyethylene terephthalate film in the form of a layer such that, after drying at room temperature for 48 hours, a photosensitive coating about 1 mm thick resulted. A 0.3 mm thick aluminum sheet provided with a polyurethane adhesive paint according to DE-AS 15 97 515 was placed on the free coating surface and the multilayer element was pressed in a sheet press at 100° C. for two minutes. The adhesive paint was obtained by reacting a branched polyester of adipic acid, glycerol and butylene glycol (OH group content of 5.2%) with triphenylmethane 4,4',4"-triisocyanate. The thickness of the spacers was chosen so that a 0.6 mm thick photopolymer layer was obtained after hot pressing. After the polyester film had been peeled off, the photosensitive layer was exposed imagewise for two minutes using a commercially available UVA flat lamp (emission wavelength range 320 to 400 nm, intensity 10 mW/cm²). After the non-exposed image areas had been washed out with warm water, a relief printing form was obtained.

2. 57.4 parts by weight of a hydrolyzed graft polymer having a limiting viscosity number of 10.0 ml/g in water and a degree of hydrolysis of 90.6%, the preparation of which has been described in DE-A 39 16 463, 37.8 parts by weight of diethylene glycol monomethyl ether acrylate, 2.0 parts by weight of trimethylolpropane triacrylate, 0.8 part by weight of 2,6-di-tert.-butyl-4-methyl-phenol, 0.005 part by weight of Fat Black HB (C.I. 26150) and 2.0 parts by weight of the sodium salt of (2,4,6-trimethyl-benzoyl)-(2'-hydroxybiphenyl-2-yl)-phosphinic acid according to Preparation Example 3 were mixed and homogenized to a transparent melt in a twin-screw extruder at 165° C. This melt was then subjected to hot pressing-between a 0.125 mm thick polyester film and a 0.3 mm thick anodically oxidized aluminum sheet, which was provided with a polyurethane coating, at 155° C. for two minutes in a sheet press to give a layer 0.8 mm thick. After the polyester film had been peeled off, the layer was exposed under a UVA flat lamp for two minutes and developed with water at 40° C. for three minutes. After drying, a relief printing plate was obtained. The hardness of the crosslinked photopolymer layer was 54 Shore A.

Use Examples 3-5

General instructions:

To prepare the aqueous paint and printing ink systems which can be cured by UV radiation and are described below, the unsaturated polymers, oligomers and monomers which can be polymerized by free radicals and are familiar to the expert were emulsified or dispersed in water with the aid of an emulsifier, if appropriate after addition of a photoinitiator from the series comprising hydroxyalkylphenones, thioxanthones, benzophenones and acylphosphane oxides, and an aqueous solution of the compound (I) according to the invention and if appropriate pigments dispersed in water or dyestuffs dissolved in water were then added.

If the photoinitiator salts dissolve in the unsaturated polymers, oligomers and monomers described or mixtures thereof, they can also be employed in 100% systems (anhydrous, solvent-free).

Curing was carried out with mercury pressure lamps (2×20 cm /100 W/cm).

| 3. UV gloss paint (aqueous) | |
|---|---|
| a) epoxy-acrylate | 46.00 |
| b) dipropylene glycol diacrylate | 11.50 |
| c) emulsifier | 2.00 |
| d) the lithium salt of (2,4,6-trimethyl-benzoyl)-(2'-hydroxy-biphenyl-2-yl)-phosphinic acid | 2.10 |
| e) water | 40.00 |

The paint films were cured at a belt speed of 1–10 m/minute. They were applied, for example, to polyester films, polycarbonate and various metal substrates, and the like.

| 4. Pigmented UV paints (aqueous) | |
|---|---|
| a) epoxy-acrylate | 39.00 |
| b) dipropylene glycol diacrylate | 13.00 |
| c) emulsifier | 2.00 |
| d) ®Borchigel DP 40 (Borchers) | 2.00 |
| e) the potassium salt of (2-methyl-benzoyl)-(2'-hydroxybiphenyl-2-yl)-phosphinic acid (Preparation Example 1) | 1.80 |
| f) water | 46.00 |

The paint films were cured at a belt speed of 1–15 m/minute, depending on the coating thickness of the paint film. They were applied as in Example 3.

Other aqueous pigment dispersions, such as ®Colanyl-Gelb FGL 130 (Hoechst) and ®Colanyl-Gelb HR 130 (Hoechst) and the like were also employed successfully in the experiments in an analogous manner.

SHEET OF FOMULAE

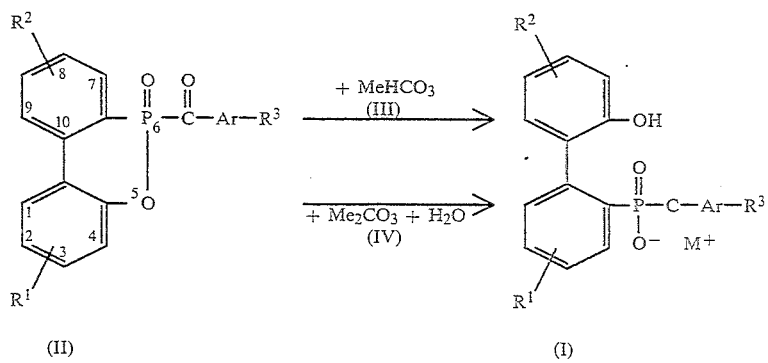

We claim:
1. An acyl-(2'-hydroxybiphenyl-2-yl)-phosphinic acid salt of the formula

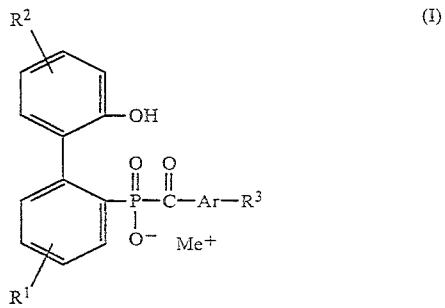

in which each of the radicals $R^1$, $R^2$ and $R^3$ can be present once or several times, and in which $R^1$ and $R^2$ independently of one another are hydrogen, an alkyl or alkoxy radical having in each case 1 to 6 carbon atoms or halogen having an atomic number of 9 to 35, $R^3$ has the same meaning as $R^1$ or $R^2$, and like $R^1$ and $R^2$, $R^3$ represents one or a plurality of substituents, Ar is an aromatic hydrocarbon radical having 6 to 10 carbon atoms and Me is a cation of at least one alkali metal or $N(R^4)_4^+$, in which the radicals $R^4$ are identical or different and are an alkyl radical having in each case 1 to 6 carbon atoms.

2. A compound as claimed in claim 1, in which at least one of the two radicals $R^1$ and $R^2$ is hydrogen.

3. A compound as claimed in claim 1, in which the radical $R^3$ is hydrogen or one to three alkyl radicals.

4. A compound as claimed in claim 1, in which a said alkyl radical is methyl or ethyl.

5. A compound as claimed in claim 1, in which the radical Ar is a benzene ring.

6. A photopolymerizable composition which comprises a compound (I) as claimed in claim 1.

7. A photopolymerizable composition as claimed in claim 6, wherein the compound (I) is present in an amount of 0.01 to 15, based on the weight of the photopolymerizable composition.

8. A coating, grouting, filler or sealing agent containing a photopolymerizable composition as claimed in claim 6, which can be cured by radiation.

9. A photopolymerizable composition as claimed in claim 6, in which the compound (I) is mixed with other photoinitiators anthone, in a weight ratio of 0.5:1 to 30:1, the total content of photoinitiators being between 1 and 20%, based on the weight of the total polymerizable composition.

10. A photopolymerizable composition as claimed in claim 9, wherein a said other photoinitiator is an aromatic ketone, a thioxanthone derivative or a combination thereof.

11. A photopolymerizable composition as claimed in claim 9, wherein said weight ratio is 0.8:1 to 10:1.

12. A photopolymerizable composition as claimed in claim 6, which additionally contains at least one accelerator.

13. A photopolymerizable composition as claimed in claim 6, wherein said compound (I) is present in an amount of from 0.1 to 5%, based on the weight of the photopolymerizable composition.

14. A clear or pigmented paint or a printing ink comprising a photopolymerizable composition as claimed in claim 6 which can be cured by radiation.

15. A photopolymerizable composition as claimed in claim 6, wherein said composition contains a secondary or tertiary amino accelerator or a combination of secondary and tertiary amino accelerators.

* * * * *